(12) United States Patent
Berry

(10) Patent No.: US 11,426,213 B1
(45) Date of Patent: Aug. 30, 2022

(54) VERTEBRAL FIXATION ASSEMBLY

(71) Applicant: Bret Michael Berry, Tallahassee, FL (US)

(72) Inventor: Bret Michael Berry, Tallahassee, FL (US)

( * ) Notice: Subject to any disclaimer, the term of this patent is extended or adjusted under 35 U.S.C. 154(b) by 0 days.

(21) Appl. No.: 17/370,502

(22) Filed: Jul. 8, 2021

(51) Int. Cl.
| | | |
|---|---|---|
| A61B 17/70 | (2006.01) | |
| A61F 2/44 | (2006.01) | |
| A61B 17/86 | (2006.01) | |
| A61B 17/56 | (2006.01) | |

(52) U.S. Cl.
CPC ...... *A61B 17/7064* (2013.01); *A61B 17/7002* (2013.01); *A61B 17/7032* (2013.01); *A61B 17/7037* (2013.01); *A61B 17/8625* (2013.01); *A61B 17/8695* (2013.01); *A61F 2/4405* (2013.01); *A61B 2017/564* (2013.01)

(58) Field of Classification Search
CPC .............. A61B 17/70; A61B 17/7023; A61B 17/7062–7071
See application file for complete search history.

(56) References Cited

U.S. PATENT DOCUMENTS

| | | | |
|---|---|---|---|
| 7,611,526 | B2 | 11/2009 | Carl |
| 8,066,771 | B2 | 11/2011 | Reiley |
| 8,123,786 | B2 | 2/2012 | Lins |
| 9,089,372 | B2 | 7/2015 | O'Neil |
| 10,105,164 | B2 | 10/2018 | Baynham |
| 2005/0149030 | A1* | 7/2005 | Serhan ............... A61B 17/7064 606/279 |
| 2006/0058790 | A1* | 3/2006 | Carl ..................... A61B 17/70 606/248 |
| 2007/0055241 | A1* | 3/2007 | Matthis ............. A61B 17/7032 606/267 |
| 2007/0088358 | A1 | 4/2007 | Yuan |
| 2009/0093851 | A1* | 4/2009 | Osman ............... A61B 17/7064 606/301 |
| 2010/0185239 | A1* | 7/2010 | Patel ................. A61B 17/7071 606/246 |
| 2011/0106168 | A1* | 5/2011 | Bucci ................ A61B 17/7032 606/264 |
| 2014/0135844 | A1* | 5/2014 | Ark .................... A61B 17/7034 606/270 |
| 2016/0361096 | A1* | 12/2016 | van der Pol ....... A61B 17/7076 |
| 2017/0189071 | A1* | 7/2017 | Fessler ............... A61B 17/7091 |

FOREIGN PATENT DOCUMENTS

WO   WO-9848717 A1 * 11/1998 ........... A61B 17/704

* cited by examiner

*Primary Examiner* — Eduardo C Robert
*Assistant Examiner* — Michelle C Eckman
(74) *Attorney, Agent, or Firm* — Ellenoff Grossman & Schole LLP; James M. Smedley; Alex Korona

(57) ABSTRACT

An apparatus configured to attach a first vertebral body and a second vertebral body is disclosed. The apparatus includes a fastener including an anchor and a polyaxial head rotatably attached to the anchor, the anchor configured to be fastened to the first vertebral body, and an anchor assembly configured to be received in an aperture of the second vertebral body. The anchor assembly is configured to be received in a head aperture of the polyaxial head. The polyaxial head has three rotational degrees of freedom relative to the anchor based on the rotatable attachment of the polyaxial head to the anchor.

7 Claims, 5 Drawing Sheets

VERTEBRAL FIXATION ASSEMBLY

TECHNICAL FIELD

The present disclosure is directed to a fixation assembly, and more particularly, to a vertebral fixation assembly.

BACKGROUND OF THE DISCLOSURE

Translaminar facet screws are utilized as a minimally invasive method to fixate two adjacent vertebral bodies. However, due to the small amount of bone on the inferior facet joint, there is a high chance that this bone itself can fracture. Pedicle screws and rods have also been used for posterior fixation of two vertebral bodies. However, whereas placing a pedicle screw through a minimally invasive incision is a relatively simple procedure, inserting a rod often involves a larger incision than for a pedicle screw. And even with this larger incision, it is often difficult and time-consuming to link the rod into pedicle screw heads.

Patent application number US20090093851 to Osman (the '851 application) discloses a translaminar facet screw connecting to a pedicle screw. As best understood, the '851 application includes a distal thread on the translaminar facet screw that threads into the pedicle screw. This arrangement involves a number of drawbacks, including that the facet screw and pedicle screw receptacle be perfectly aligned. Whereas inserting a rod into a polyaxial pedicle screw is difficult, threading a screw from the opposing side into a fixed pedicle screw is extremely difficult.

Additionally, by threading the translaminar facet screw into the pedicle screw head as disclosed in the '851 application, such threading typically acts like a lag screw, pulling the superior vertebrae into the inferior vertebrae. Whereas this may seem desirable by possibly providing compression on a potential interbody device, such threading may actually be counterproductive because introducing a lag force at the facet joint will actually likely twist the superior vertebrae. This action is unlike the linear compression of a rod-pedicle system that creates compression axially. With a lag force on the facet, the superior vertebrae rotates about the facet joint, which is located inferior of the body itself. This force places the body out of alignment with the axis of the natural spine, thereby creating scoliosis.

The exemplary disclosed system, apparatus, and method of the present disclosure is directed to overcoming one or more of the shortcomings set forth above and/or other deficiencies in existing technology.

SUMMARY OF THE DISCLOSURE

In one exemplary aspect, the present disclosure is directed to an apparatus configured to attach a first vertebral body and a second vertebral body. The apparatus includes a fastener including an anchor and a polyaxial head rotatably attached to the anchor, the anchor configured to be fastened to the first vertebral body, and an anchor assembly configured to be received in an aperture of the second vertebral body. The anchor assembly is configured to be received in a head aperture of the polyaxial head. The polyaxial head has three rotational degrees of freedom relative to the anchor based on the rotatable attachment of the polyaxial head to the anchor.

In another aspect, the present disclosure is directed to a method for attaching a first vertebral body and a second vertebral body. The method includes providing a fastener including an anchor and a polyaxial head rotatably attached to the anchor, implanting the anchor in the first vertebral body, providing an anchor assembly, making an aperture in the second vertebral body, rotating the polyaxial head in three rotational degrees of freedom relative to the anchor, and inserting the anchor assembly in both the aperture of the second vertebral body and a head aperture of the polyaxial head.

BRIEF DESCRIPTION OF THE DRAWINGS

Accompanying this written specification is a collection of drawings of exemplary embodiments of the present disclosure. One of ordinary skill in the art would appreciate that these are merely exemplary embodiments, and additional and alternative embodiments may exist and still within the spirit of the disclosure as described herein.

DETAILED DESCRIPTION AND INDUSTRIAL APPLICABILITY

The exemplary disclosed system, apparatus, and method may include a vertebral fixation assembly. In at least some exemplary embodiments, the exemplary disclosed system, apparatus, and method may provide for translaminar facet pedicle fixation. For example, the exemplary disclosed system, apparatus, and method may include a translaminar facet anchor. In at least some exemplary embodiments, the exemplary disclosed translaminar facet anchor may attach to a pedicle screw in order to affix a joint.

Figure 1:
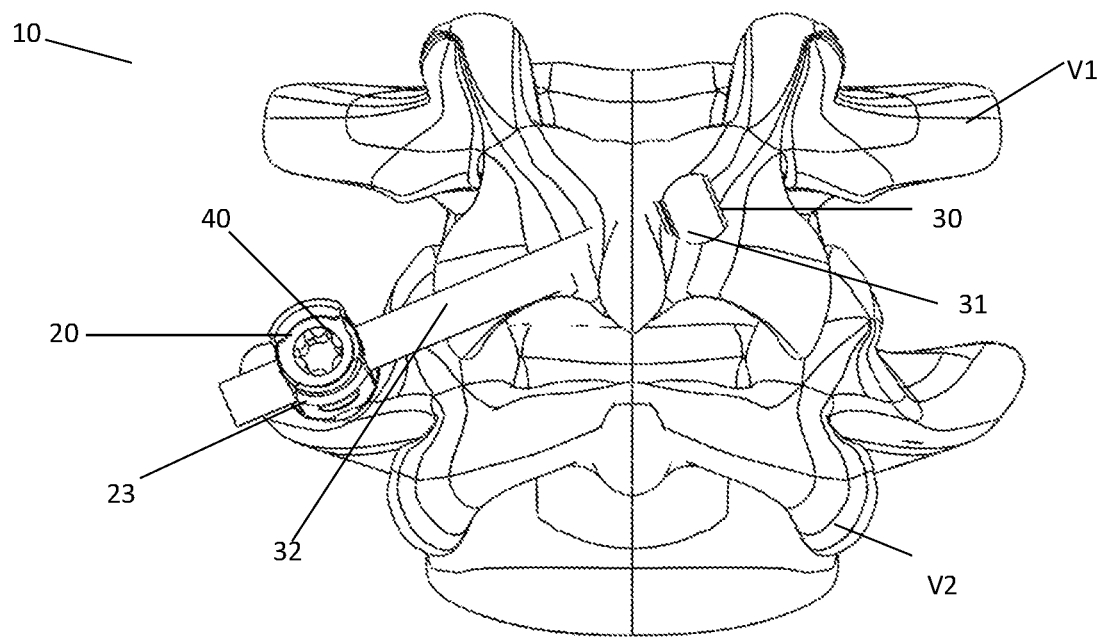
FIG. 1 illustrates a cranial view of a first exemplary embodiment.
Figure 2:
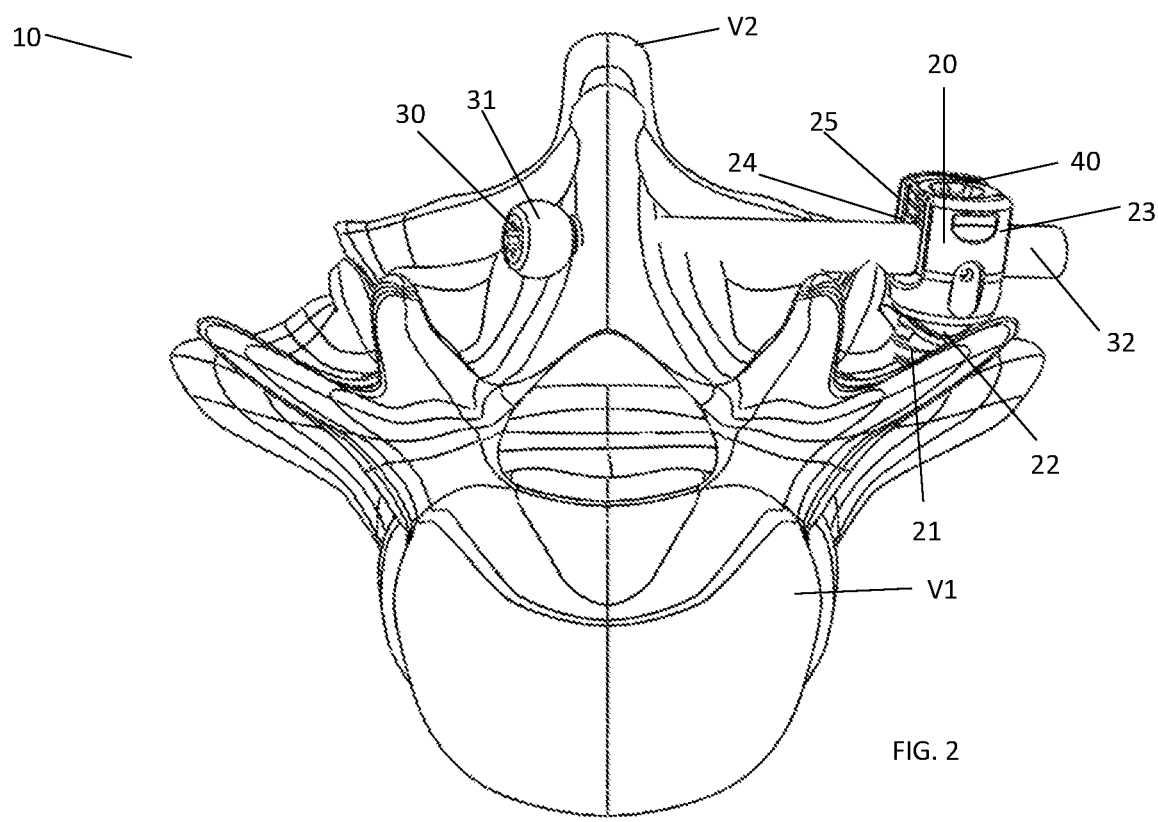
FIG. 2 illustrates a dorsal view of the first exemplary embodiment.
Figure 3:
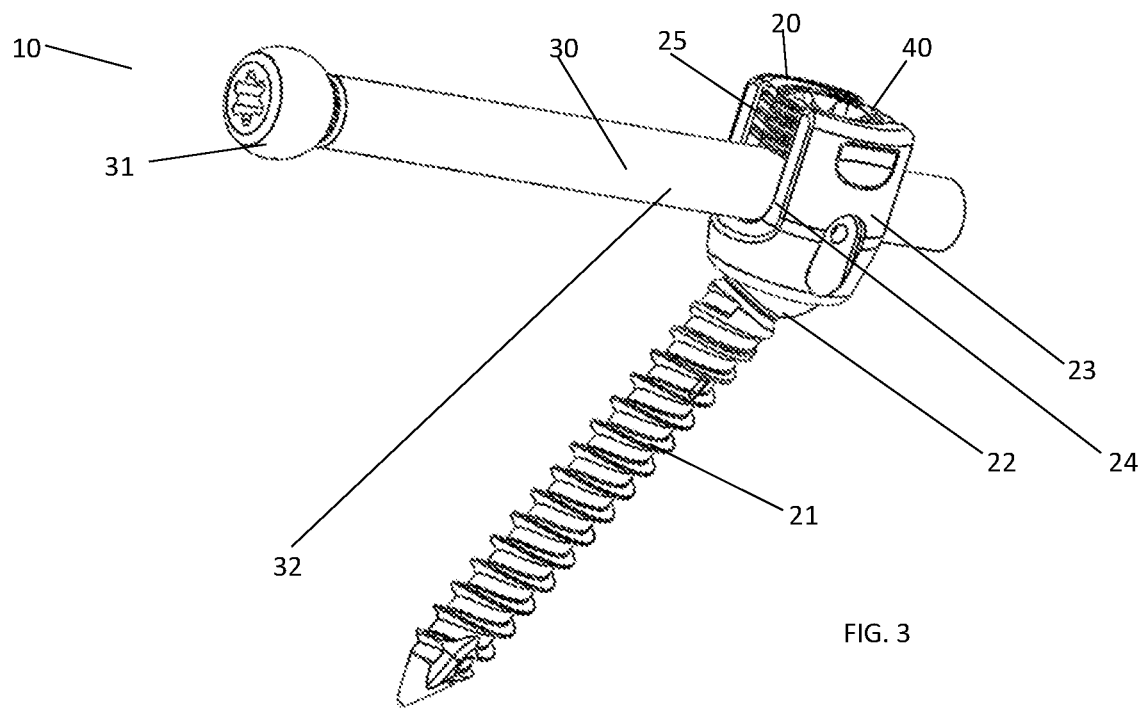
FIG. 3 illustrates a perspective view of the first exemplary embodiment.

FIGS. 1-3 illustrate a first exemplary embodiment of the exemplary disclosed system, apparatus, and method. System 10 may include at least one fastener such as a pedicle screw 20, at least one anchor assembly such as a translaminar facet anchor 30, and at least one set screw 40.

Pedicle screw 20 may include an anchor such as a threaded distal anchor 21 having a spherical head 22. Threaded distal anchor 21 may be a threaded screw. A polyaxial head 23 may be disposed on (e.g., sit on) spherical head 22, and may be able to rotate about polyaxial head 23. Based on the rotational connection of polyaxial head 23 to spherical head 22, polyaxial head 23 may be rotatable in any direction relative to spherical head 22. The attachment of polyaxial head 23 to spherical head 22 may be a triaxial joint. In at least some exemplary embodiments, the connection of polyaxial head 23 to spherical head 22 may provide the full degrees of freedom of a ball joint such as a ball and socket joint (e.g., allowing rotation in substantially all directions). For example, polyaxial head 23 may include a cavity (e.g., a socket) configured to receive spherical head 22 (e.g., a ball) to form a ball and socket joint. The connection of polyaxial head 23 to spherical head 22 may provide three rotational degrees of freedom. For example, the connection of polyaxial head 23 to spherical head 22 may provide an axial motion (e.g., twist) as a first degree of freedom and also spherical motion (e.g., swing) as second and third degrees of freedom (e.g., that may determine direction).

Polyaxial head 23 may include any suitable aperture such as a u-shaped hole 24. Polyaxial head 23 may also include a proximal threaded portion 25. Pedicle screw 20 may be fastened to (e.g., screwed into) vertebrae V2. In at least some exemplary embodiments, pedicle screw 20 may be implanted into the pedicle of inferior vertebrae V2.

An aperture (e.g., a hole) may be drilled into the lamina of the adjacent vertebrae V1 starting at the contralateral side of pedicle screw 20 (e.g., starting on the contralateral side from the pedicle screw 20). The hole may extend through the lamina and the facet joint (e.g., through a thickness of the lamina and the facet joint) for example as illustrated in FIGS. 1-3. The hole may extend to (e.g., open at) pedicle screw 20. For example, the hole may be a predrilled hole. Translaminar facet anchor 30 may then be inserted into the predrilled hole.

Translaminar facet anchor 30 may include a head 31 and a cylindrical portion such as a cylindrical rod 32. Head 31 may have a larger width (e.g., diameter) than a width (e.g., diameter) of cylindrical rod 32. A distal portion of cylindrical rod 32 may extend out of the predrilled hole and into u-shaped hole 24 of pedicle screw 20. A set screw 40 may then be inserted into threaded portion 25 of pedicle screw 20. Set screw 40 may be disposed against or onto cylindrical rod 32 of translaminar facet anchor 30. Set screw 40 may be tightened against cylindrical rod 32 disposed in u-shaped hole 24, thereby locking system 10 in place (e.g., by locking translaminar facet anchor 30 relative to pedicle screw 20). Two vertebrae (e.g., vertebrae V1 and V2) may thereby be fixed together via system 10 while maintaining their natural alignment.

Figure 4:
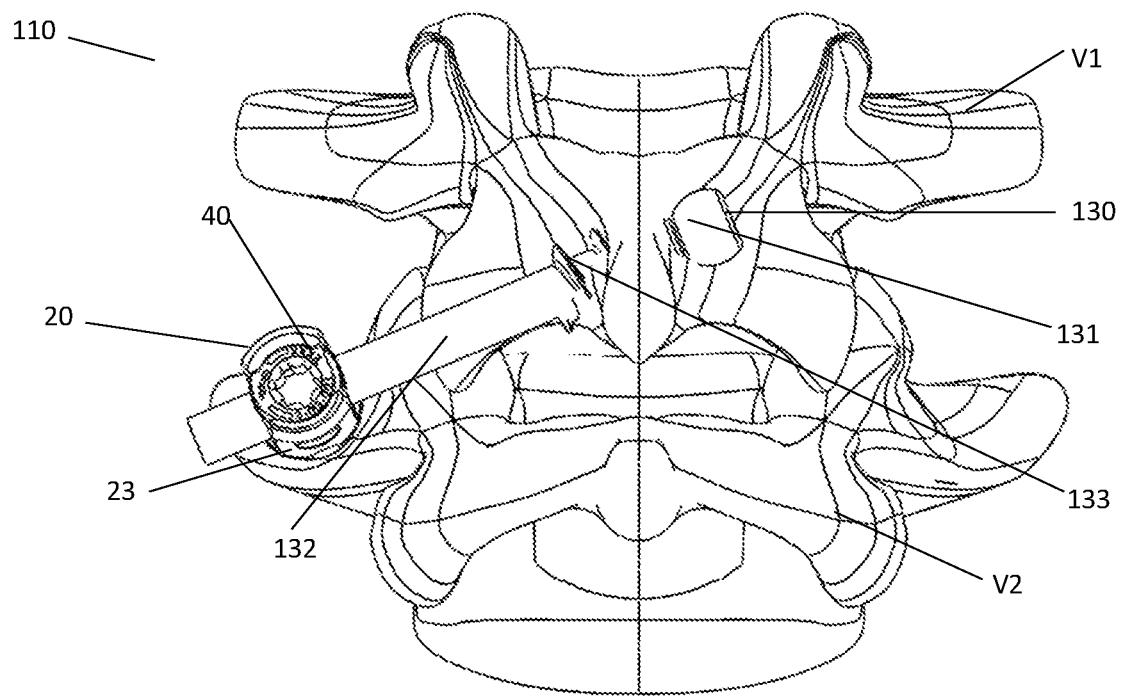
FIG. 4 illustrates a cranial view of a second exemplary embodiment.
Figure 5:
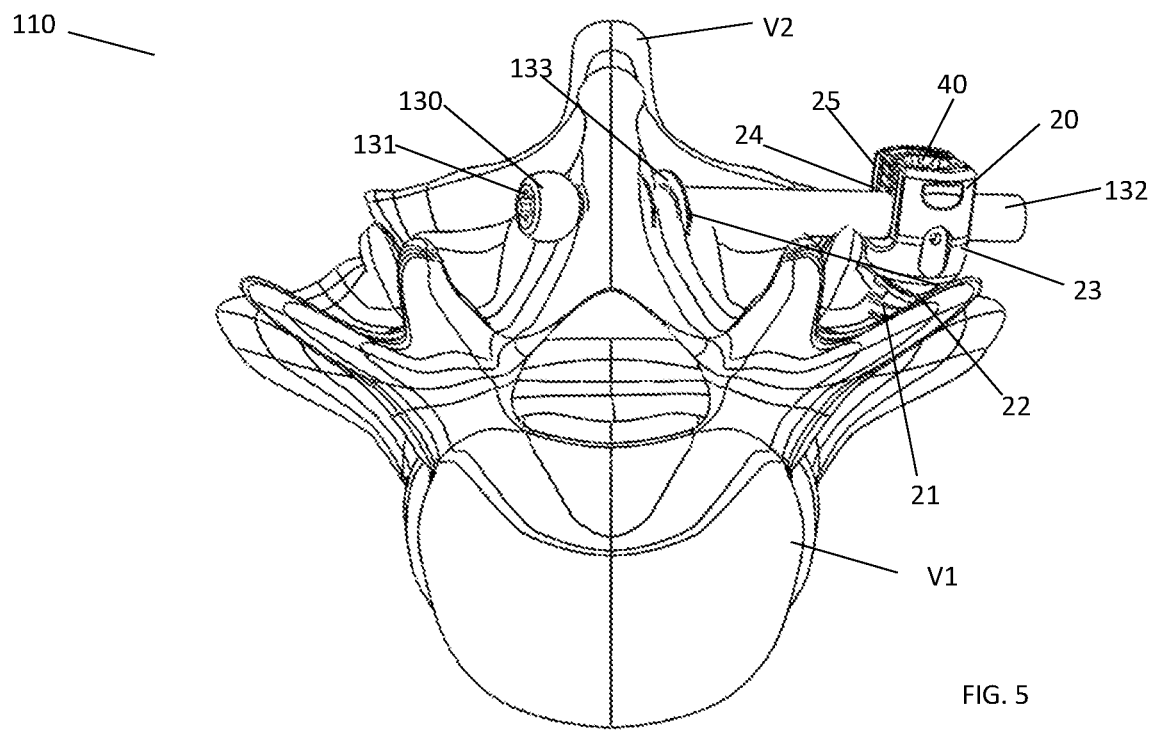
FIG. 5 illustrates a dorsal view of the second exemplary embodiment.
Figure 6:
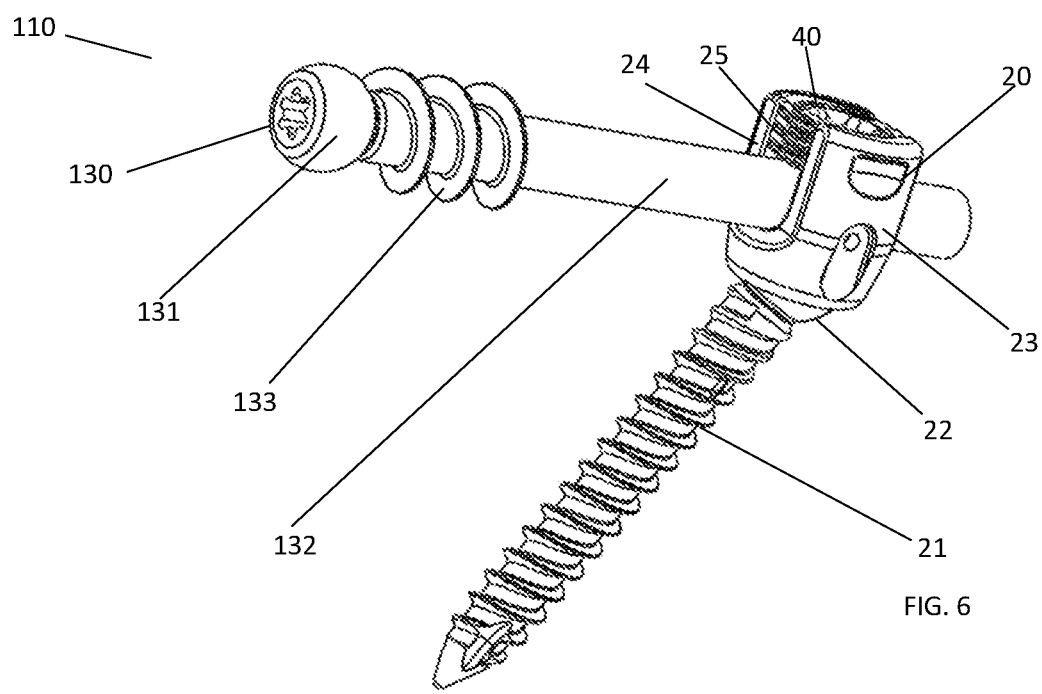
FIG. 6 illustrates a perspective view of the second exemplary embodiment.

FIGS. 4-6 illustrate a second exemplary embodiment of the exemplary disclosed system, apparatus, and method. System 110 may include at least one pedicle screw 20, at least one translaminar facet anchor 130, and at least one set screw 40.

Pedicle screw 20 may include threaded distal anchor 21 having spherical head 22. Polyaxial head 23 may be disposed on (e.g., sit on) spherical head 22, and may be able to rotate about polyaxial head 23. Polyaxial head 23 may include any suitable aperture such as u-shaped hole 24. Polyaxial head 23 may also include proximal threaded portion 25. In at least some exemplary embodiments, pedicle screw 20 may be implanted into the pedicle of inferior vertebrae V2.

A hole may be drilled into the lamina of the adjacent vertebrae V1 starting at the contralateral side of pedicle screw 20 (e.g., starting on the contralateral side from the pedicle screw 20). The hole may extend through the lamina and the facet joint (e.g., through a thickness of the lamina and the facet joint) for example as illustrated in FIGS. 4-6. The hole may extend to (e.g., open at) pedicle screw 20. For example, the hole may be a predrilled hole. Translaminar facet anchor 130 may then be inserted into the predrilled hole.

Translaminar facet anchor 130 may include a head 131, a cylindrical rod 132 portion, and a threaded proximal portion 133. Threaded proximal portion 133 may be for example a helical portion such as a helical blade (e.g., helical screw blade) that may be disposed on cylindrical rod 132. In at least some exemplary embodiments, threaded proximal portion 133 may be disposed at a portion of cylindrical rod 132 that is adjacent to head 131. For example, threaded proximal portion 133 may be disposed at a portion of cylindrical rod 132 that is distal from pedicle screw 20 when system 110 is locked in place for example as described below and as illustrated in FIGS. 4 and 5. Threaded proximal portion 133 may thread into the lamina of the superior vertebrae V1. Distal cylindrical rod 132 may extend out of the predrilled hole and into u-shaped hole 24 of pedicle screw 20.

Set screw 40 may then be inserted into threaded portion 25 of pedicle screw 20. Set screw 40 may be disposed against or onto cylindrical rod 132 of translaminar facet anchor 130. Set screw 40 may be tightened against cylindrical rod 132 disposed in u-shaped hole 24, thereby locking system 110 in place (e.g., by locking translaminar facet anchor 130 relative to pedicle screw 20). Two vertebrae (e.g., vertebrae V1 and V2) may thereby be fixed together via system 110 while maintaining their natural alignment.

Figure 7:
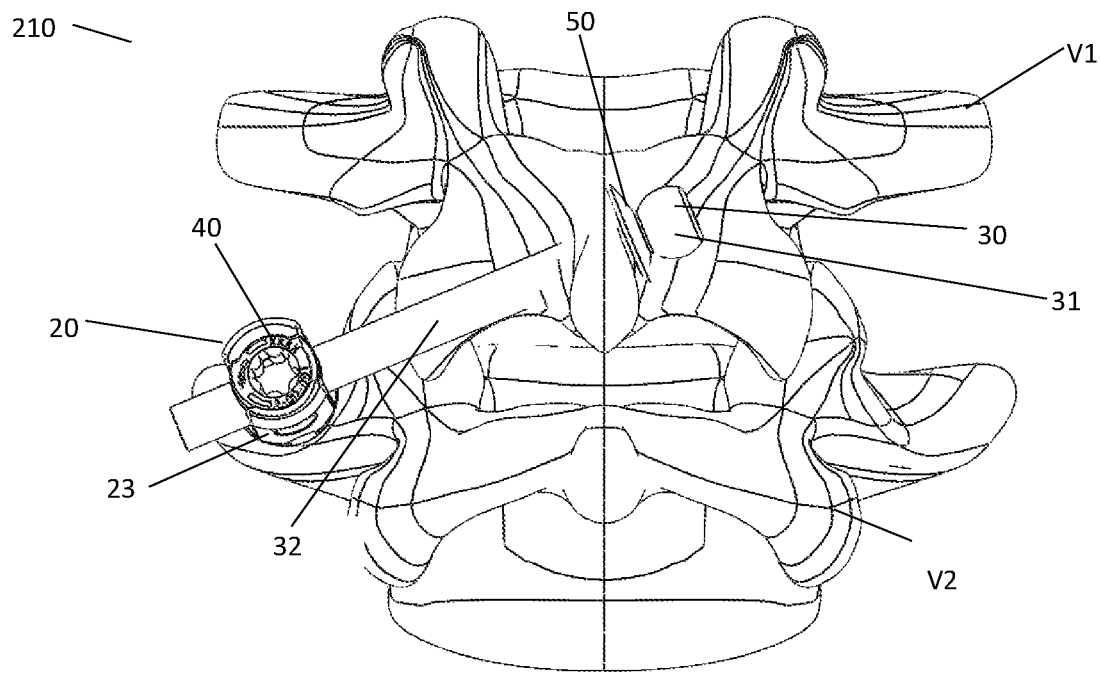
FIG. 7 illustrates a cranial view of a third exemplary embodiment.
Figure 8:
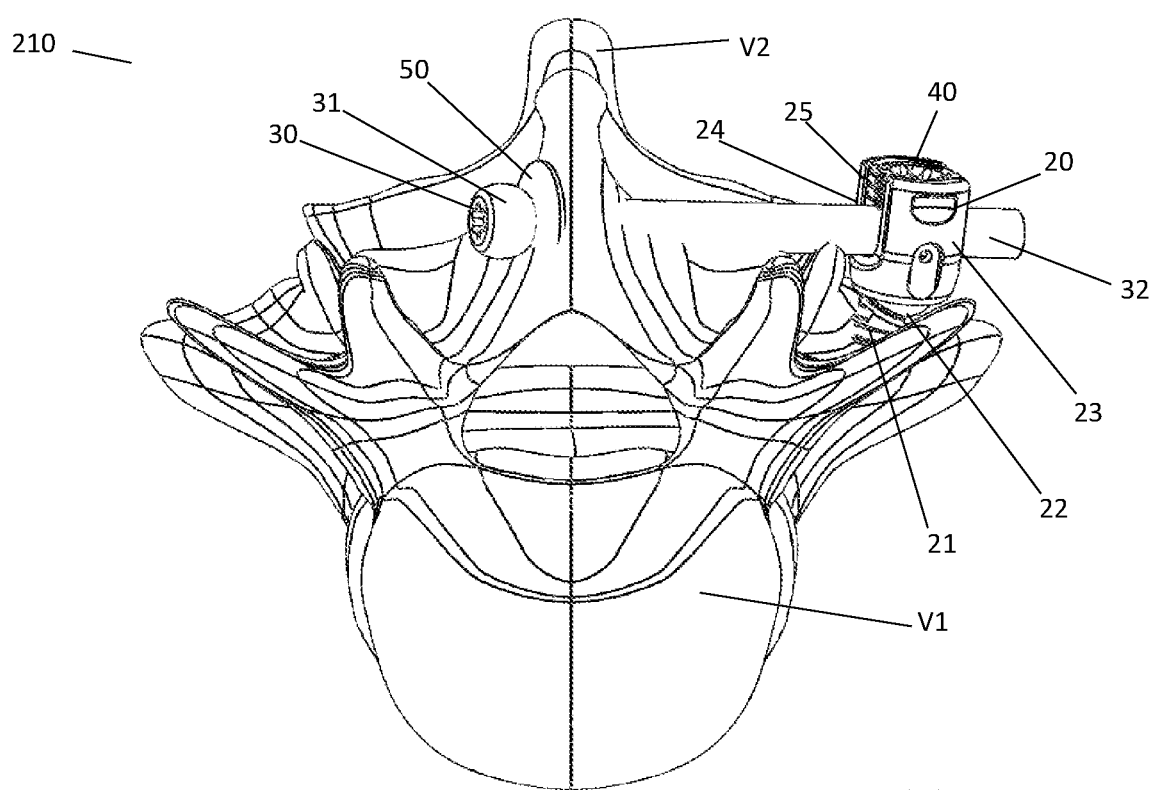
FIG. 8 illustrates a dorsal view of the third exemplary embodiment.
Figure 9:
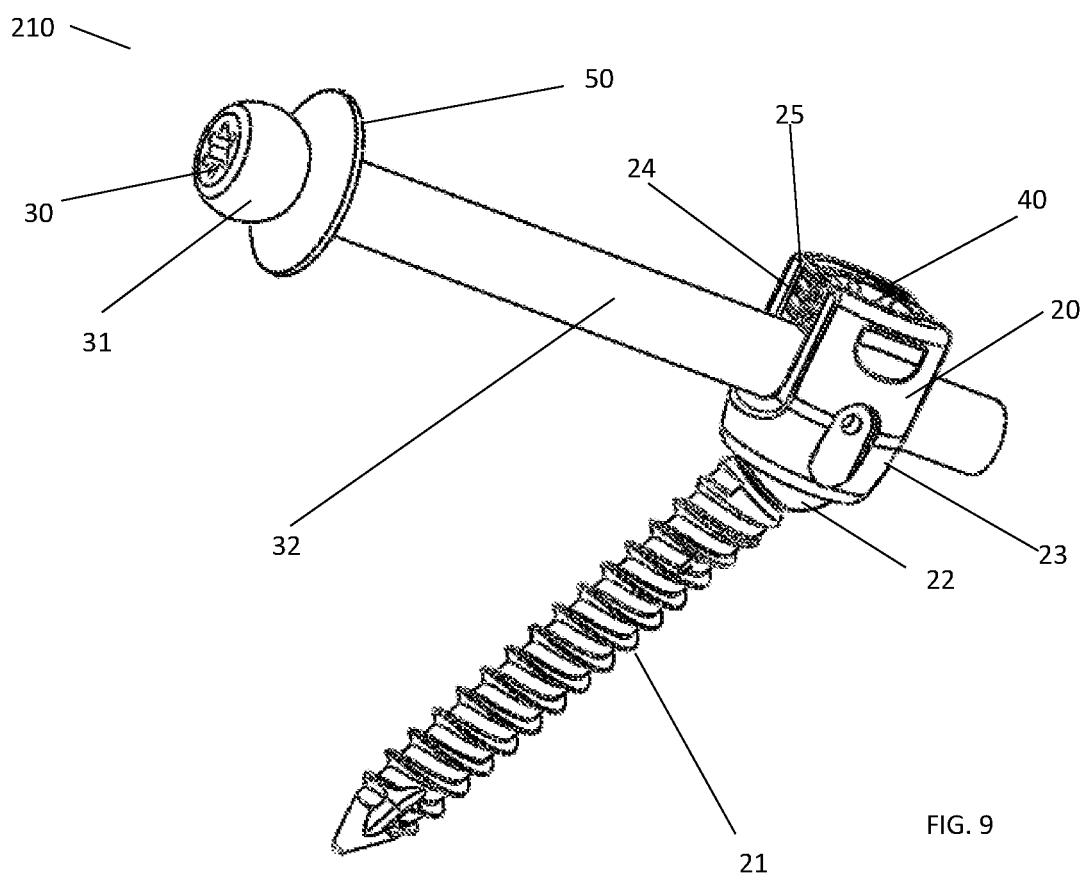
FIG. 9 illustrates a perspective view of the third exemplary embodiment.

FIGS. 7-9 illustrate a third exemplary embodiment of the exemplary disclosed system, apparatus, and method. System 210 may include at least one pedicle screw 20, at least one translaminar facet anchor 30 (e.g., or translaminar facet anchor 130), at least one set screw 40, and at least one washer 50.

Pedicle screw 20 may include threaded distal anchor 21 having spherical head 22. Polyaxial head 23 may be disposed on (e.g., sit on) spherical head 22, and may be able to rotate about polyaxial head 23. Polyaxial head 23 may include any suitable aperture such as u-shaped hole 24. Polyaxial head 23 may also include proximal threaded portion 25. In at least some exemplary embodiments, pedicle screw 20 may be implanted into the pedicle of inferior vertebrae V2.

A hole may be drilled into the lamina of the adjacent vertebrae V1 starting at the contralateral side of pedicle screw 20 (e.g., starting on the contralateral side from the pedicle screw 20). The hole may extend through the lamina and the facet joint (e.g., through a thickness of the lamina and the facet joint) for example as illustrated in FIGS. 7-9. The hole may extend to (e.g., open at) pedicle screw 20. For example, the hole may be a predrilled hole. Translaminar facet anchor 30 (e.g., or translaminar facet anchor 130) may then be inserted into the predrilled hole.

Translaminar facet anchor 30 may include washer 50 that may be configured to fit over cylindrical rod 32. For example, washer 50 may be configured to fit over cylindrical rod 32 just distal of head 31. Translaminar facet anchor 30 may include head 31 and a cylindrical portion such as a cylindrical rod 32. Distal cylindrical rod 32 may extend out of the exemplary disclosed predrilled hole and into u-shaped hole 24 of the pedicle screw 20. Washer 50 may contact or abut against (e.g., rest against) the spinous process of the superior vertebrae V1. Washer 50 may thereby contribute to securing a position of translaminar facet anchor 30 relative to the spinous process of the superior vertebrae V1 and to pedicle screw 20.

Set screw 40 may then be inserted into threaded portion 25 of pedicle screw 20. Set screw 40 may be disposed against or onto cylindrical rod 32 of translaminar facet anchor 30 (e.g., or cylindrical rod 132 of translaminar facet anchor 130). Set screw 40 may be tightened against cylindrical rod 32 disposed in u-shaped hole 24, thereby locking system 210 in place (e.g., by locking translaminar facet anchor 30 relative to pedicle screw 20). Two vertebrae (e.g., vertebrae V1 and V2) may thereby be fixed together via system 210 while maintaining their natural alignment.

The exemplary disclosed fixation assembly may be formed from any suitable material for providing fixation of vertebral bodies such as, for example, metal (e.g., titanium, stainless steel, cobalt-based metal, and/or any other suitable metal material), plastic, ceramic, and/or any other suitable structural materials for providing a fixation assembly.

In at least some exemplary embodiments, the exemplary disclosed system, apparatus, and method may include a polyaxial head pedicle screw that may be inserted into the pedicle of the inferior vertebrae of a pair of adjacent vertebrae that are desired to be fused. A hole may then be drilled translaminally through the superior vertebral, starting from the oppose side (e.g., opposite side) of the pedicle screw, towards the pedicle screw head, and, through the facet joint. The translaminar facet anchor may be a rod with a head, and may be inserted through the translaminar hole and into the polyaxial head of the pedicle screw. A set screw may then be inserted into the top of the pedicle screw head, locking the translaminar facet anchor into place, and thereby fixating the two vertebral bodies (e.g., relative to each other). Alternatively for example, the translaminar facet anchor may have threads that may be disposed proximally towards the head to thread into the superior lamina.

The exemplary disclosed system, apparatus, and method may be used in any suitable application involving a surgical procedure (e.g., on a human or animal). For example, the exemplary disclosed system, apparatus, and method may be used in any suitable application involving vertebral surgeries or procedures. The exemplary disclosed system, apparatus, and method may be used in any suitable application for fixating adjacent vertebral bodies. The exemplary disclosed system, apparatus, and method may be used in any suitable application for pedicle fixation such as translaminar facet pedicle fixation.

In at least some exemplary embodiments, the exemplary disclosed apparatus may be configured to attach a first vertebral body and a second vertebral body. The exemplary disclosed apparatus may include a fastener including an anchor and a polyaxial head rotatably attached to the anchor, the anchor configured to be fastened to the first vertebral body, and an anchor assembly configured to be received in an aperture of the second vertebral body. The anchor assembly may be configured to be received in a head aperture of the polyaxial head. The polyaxial head may include three rotational degrees of freedom relative to the anchor based on the rotatable attachment of the polyaxial head to the anchor. An elongated shaft of the anchor assembly may include a helical blade. The exemplary disclosed apparatus may also include a washer disposed on an elongated shaft of the anchor assembly. The head aperture may be a u-shaped aperture. The anchor of the fastener may be a threaded screw. The anchor assembly may include an elongated shaft configured to be received in the head aperture. The exemplary disclosed apparatus may further include a head having a larger diameter than a diameter of the elongated shaft, the head attached to an end portion of the elongated shaft. The head aperture may include a threaded portion. The exemplary disclosed apparatus may also include a set screw configured to be received in the threaded portion, the set screw configured to be tightened against the anchor assembly when the anchor assembly is received in the head aperture.

In at least some exemplary embodiments, the exemplary disclosed method may be for attaching a first vertebral body and a second vertebral body. The exemplary disclosed method may include providing a fastener including an anchor and a polyaxial head rotatably attached to the anchor, implanting the anchor in the first vertebral body, providing an anchor assembly, making an aperture in the second vertebral body, rotating the polyaxial head in three rotational degrees of freedom relative to the anchor, and inserting the anchor assembly in both the aperture of the second vertebral body and a head aperture of the polyaxial head. Implanting the anchor in the first vertebral body may include screwing the anchor into the first vertebral body. Screwing the anchor into the first vertebral body may include screwing the anchor that is a pedicle screw into the pedicle of the first vertebral body that is the vertebrae V2. Making the aperture in the second vertebral body may include drilling into the lamina of the second vertebral body. Drilling into the lamina of the second vertebral body may include drilling translaminally through the second vertebral body that is the vertebrae V1. The first vertebral body may be the vertebrae V2 and the second vertebral body may be the vertebrae V1. The exemplary disclosed method may also include disposing a set screw in a threaded portion of the head aperture, and tightening the set screw against the anchor assembly when the anchor assembly is inserted in the head aperture.

In at least some exemplary embodiments, the exemplary disclosed apparatus may be configured to attach a first vertebral body and a second vertebral body. The exemplary disclosed apparatus may include a fastener including a threaded screw, which includes a spherical head, and a polyaxial head attached to the spherical head, the threaded screw configured to be fastened to the first vertebral body, and an anchor assembly configured to be received in an aperture of the second vertebral body. The anchor assembly may include an elongated shaft that is configured to be received in a head aperture of the polyaxial head. The polyaxial head may include a socket configured to rotatably receive the spherical head, the socket and the spherical head forming a ball and socket joint between the threaded screw and the polyaxial head. The exemplary disclosed apparatus may also include a head having a larger diameter than a diameter of the elongated shaft, the head attached to an end portion of the elongated shaft. The exemplary disclosed apparatus may further include a helical blade disposed on the elongated shaft adjacent to the head. The exemplary disclosed apparatus may also include a washer disposed on the elongated shaft adjacent to the head.

The exemplary disclosed system, apparatus, and method may provide an efficient and effective technique for fixating two adjacent vertebral bodies. The exemplary disclosed system, apparatus, and method may substantially avoid time-intensive linking of a rod into pedicle screw heads. The exemplary disclosed system, apparatus, and method may provide for fixation of adjacent vertebral bodies without causing twisting or rotation of vertebrae relative to each other.

While multiple embodiments are disclosed, still other embodiments of the present disclosure will become apparent to those skilled in the art from this detailed description. There may be aspects of this disclosure that may be practiced without the implementation of some features as they are described. It should be understood that some details have not been described in detail in order to not unnecessarily obscure the focus of the disclosure. The disclosure is capable of myriad modifications in various obvious aspects, all without departing from the spirit and scope of the present disclosure. Accordingly, the drawings and descriptions are to be regarded as illustrative rather than restrictive in nature.

What is claimed is:

1. An apparatus configured to attach a first vertebral body and a second vertebral body, comprising:

a fastener including an anchor and a polyaxial head rotatably attached to the anchor, the anchor configured to be fastened to the first vertebral body and the polyaxial head being formed with a head aperture that is open to a top portion of the polyaxial head; and an anchor assembly having an elongated shaft including a first end formed with a head portion and a helical blade and a second end having a smooth surface, the first end of the elongated shaft being received at an aperture of the second vertebral body and the second end of the elongated shaft configured to be received in the head aperture of the polyaxial head;

wherein the helical blade abuts the head portion of the elongated shaft and terminates before a midpoint of the elongated shaft and the helical blade has a diameter that is greater than or equal to a diameter of the head portion of the elongated shaft;

wherein the polyaxial head has three rotational degrees of freedom relative to the anchor based on the rotatable attachment of the polyaxial head to the anchor.

2. The apparatus of claim 1, wherein the anchor of the fastener is a threaded screw.

3. The apparatus of claim 1, further comprising a washer disposed on an elongated shaft of the anchor assembly.

4. The apparatus of claim 1, wherein the head aperture forms a U-shaped channel in the polyaxial head.

5. The apparatus of claim 1, wherein the diameter of the head portion of the elongated shaft is greater than a diameter of the elongated shaft.

6. The apparatus of claim 1, wherein the head aperture includes a threaded portion.

7. The apparatus of claim 6, further comprising a set screw configured to be received in the threaded portion, the set screw configured to be tightened against the anchor assembly when the anchor assembly is received in the head aperture.

* * * * *